(12) United States Patent
Sun (10) Patent No.: US 9,846,671 B2
(45) Date of Patent: Dec. 19, 2017

(54) BIDIRECTIONAL DATA TRANSMISSION SYSTEM

(71) Applicants:Qingdao Hisense Electronics Co., Ltd., Qingdao, Shandong (CN); Hisense USA Corp., Suwanee, GA (US); Hisense International Co., Ltd., Qingdao, Shandong (CN)

(72) Inventor: Xuebin Sun, Qingdao (CN)

(73) Assignees: Qingdao Hisense Electronics Co., Ltd., Qingdao (CN); Hisense USA Corp., Suwanee, GA (US); Hisense International Co., Ltd., Qingdao (CN)

( * ) Notice: Subject to any disclaimer, the term of this patent is extended or adjusted under 35 U.S.C. 154(b) by 290 days.

(21) Appl. No.: 14/577,289

(22) Filed: Dec. 19, 2014

(65) Prior Publication Data

US 2015/0370746 A1    Dec. 24, 2015

(30) Foreign Application Priority Data

Jun. 23, 2014    (CN) .......................... 2014 1 0283829

(51) Int. Cl.
   *G06F 13/42*    (2006.01)
   *G06F 13/40*    (2006.01)
(52) U.S. Cl.
   CPC ...... *G06F 13/4221* (2013.01); *G06F 13/4022* (2013.01)
(58) Field of Classification Search
   CPC .. G06F 13/40; G06F 13/4022; G06F 13/4068; G06F 13/4282
   USPC ........................................ 710/106, 107, 301
   See application file for complete search history.

(56) References Cited

U.S. PATENT DOCUMENTS

| | | | |
|---|---|---|---|
| 8,312,199 B2* | 11/2012 | Johnson .............. | G06F 13/4022 710/16 |
| 8,923,063 B2* | 12/2014 | Shim ...................... | G11C 16/22 365/185.18 |
| 2005/0094591 A1 | 5/2005 | Kwon | |

(Continued)

FOREIGN PATENT DOCUMENTS

| | | |
|---|---|---|
| CN | 2561168 Y | 7/2003 |
| CN | 101655825 A | 2/2010 |

(Continued)

OTHER PUBLICATIONS

First Chinese Office Action corresponding to Chinese Application No. 201410283829.7 dated Aug. 3, 2016 and English translation, (9p).

*Primary Examiner* — Brian Misiura
(74) *Attorney, Agent, or Firm* — Brinks Gilson & Lione (57) ABSTRACT

A system for bidirectional signal transmission may comprise a forward data transmission circuit to unidirectionally transmit a first input signal and a backward data transmission circuit to unidirectionally transmit a second input signal. The backward data transmission circuit may comprises a logic circuit to detect a voltage difference over a resistance element in the forward data transmission circuit. When the voltage difference is lower than a threshold value, the logic circuit outputs a first voltage level. When the voltage difference is greater than or equal to a threshold value, the logic circuit outputs a second voltage level different from the first voltage level.

20 Claims, 4 Drawing Sheets

(56) References Cited

U.S. PATENT DOCUMENTS

2015/0293879 A1* 10/2015 Yi ..................... G06F 13/4068
710/106

FOREIGN PATENT DOCUMENTS

| CN | 102638338 A | 8/2012 |
|----|-------------|--------|
| JP | 61245697 A | 10/1986 |

* cited by examiner

702. Receiving, by the forward data transmission circuit, the first signal from the first input port and unidirectionally transmitting the first signal to the first output port 704. Receiving, by the backward data transmission circuit, the second signal from the second input port to generate a voltage difference over a resistance element of the first data transmission circuit, and detecting, by a logic circuit in the second data transmission circuit, a voltage difference over a resistance element in the first data transmission circuit 706. Modifying, by the backward data transmission circuit, the second input signal 708. Generating, by the backward data transmission circuit, the output signal, wherein when the voltage difference is lower than a threshold value, the logic circuit outputs the first voltage level, when the voltage difference is greater than or equal to the threshold value, the logic circuit outputs the second voltage level different from the first voltage level

Fig. 7

BIDIRECTIONAL DATA TRANSMISSION SYSTEM

PRIORITY STATEMENT

This application claims priority to Chinese Patent Application No. 201410283829.7, filed on Jun. 23, 2014, which is hereby incorporated by reference in its entirety.

TECHNICAL FIELD

The present disclosure generally relates to data transmission technology. Specifically, the present disclosure relates to a system for bidirectional data transmission.

BACKGROUND

Data transmission is an important technology widely used in electronic devices. Almost every computer, cellphone, or tablet devices has adopted I/O (input/output) ports, such as a USB (Universal Serial Bus), to transmit data from and to an external device. The external device may be an external storage device, a mouse, a camera, or a smart device such as a computer. As the performances of these electronic devices are constantly improved, the I/O ports therein are required to support faster and faster data transmission. Sometimes such requirement means a new design of the I/O ports. For example, compared to USB 2.0, which includes only one pair of differential data transmission lines, a new generation USB 3.0 includes three pairs of differential data transmission line. But upgrading hardware is expensive. And newly designed I/O ports generally are only applicable to newly manufactured device. Manufactures are will generally unable to recall and upgrade electronic devices. Thus an alternative and cheaper option to achieve a higher data transmission speed may be to increase I/O ports' transmission efficiency based on the old designs.

SUMMARY

The present disclosure relates to a bidirectional data transmission system. Using a same transmission line, the system may be able to transmit data in both forward and backward direction. The backward data transmission does not depend on whether an input signal in the forward direction is on a high voltage level or a low voltage level.

According to an aspect of the present disclosure, a system for bidirectional signal transmission may comprise a forward data transmission circuit to unidirectionally transmit a first input signal and a backward data transmission circuit to unidirectionally transmit a second input signal. The backward data transmission circuit may comprise a logic circuit to detect a voltage difference over a resistance element in the forward data transmission circuit. When the voltage difference is lower than a threshold value, the logic circuit outputs a first voltage level. When the voltage difference is greater than or equal to a threshold value, the logic circuit outputs a second voltage level different from the first voltage level.

According to another aspect of the present disclosure, a method for bidirectional data transmission may comprises receiving, by a forward data transmission circuit, a first input signal from a first input port and unidirectionally transmitting the first input signal to a first output port; receiving, by a backward data transmission circuit, a second input signal from a second input port to generate a voltage difference over a resistance element of the forward data transmission circuit; detecting, by a logic circuit in the backward data transmission circuit, a voltage difference over a resistance element in the forward data transmission circuit; and generating, by the backward data transmission circuit, an output signal, wherein when the voltage difference is lower than a threshold value, the logic circuit outputs a first voltage level, when the voltage difference is greater than or equal to a threshold value, the logic circuit outputs a second voltage level different from the first voltage level.

DETAILED DESCRIPTION

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. The following detailed description is, therefore, not intended to be limiting on the scope of what is claimed.

Reference throughout this specification to "embodiments," "an embodiment," "example embodiment," or the like in the singular or plural means that one or more particular features, structures, or characteristics described in connection with an embodiment is included in at least embodiments of the present disclosure. Thus, the appearances of the phrases "in embodiments" or "in an embodiment," "in an example embodiment," or the like in the singular or plural in various places throughout this specification are not necessarily all referring to the same embodiment. Furthermore, the particular features, structures, or characteristics may be combined in any suitable manner in one or more embodiments.

In general, terminology may be understood at least in part from usage in context. For example, terms, such as "and", "or", or "exclusive-OR," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

As used herein, the term "module" or "unit" may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module or unit may include memory (shared, dedicated, or group) that stores code executed by the processor.

Figure 1:
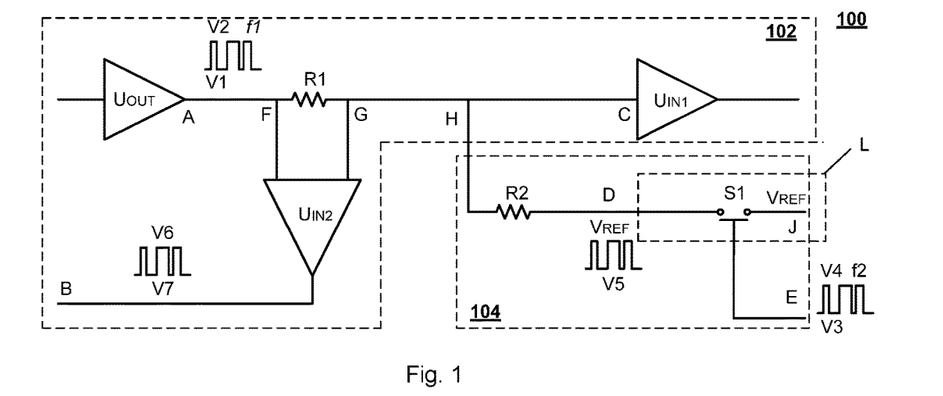
FIG. 1 illustrates a bidirectional data transmission system according to example embodiments of the present disclosure.

FIG. 1 illustrates a data transmission system 100 for bidirectional data transmission according to example embodiments of the present disclosure.

The data transmission system 100 may include a forward data transmission circuit A-F-G-H-C, where A may be a first input port and C may be a first output port. The forward data transmission circuit A-F-G-H-C may be configured to unidirectionally transmit a data stream (i.e., an input signal) from the first input port A to the first output port C.

To this end, the forward data transmission circuit A-F-G-H-C may include, along a forward direction from the first input port A to the first output port C, an input buffer circuit $U_{OUT}$, a first resistance element $R_1$ and an output buffer circuit $U_{IN1}$. The input buffer circuit $U_{OUT}$, first resistance element $R_1$ and output buffer circuit $U_{IN1}$ may be connected in series. The first resistance element $R_1$ may be a resistor or other circuit that may be characterized with a resistance. The buffer circuit $U_{OUT}$ may be a voltage buffer amplifier, which has high (1 MΩ to 10 TΩ) input impedance and low output impedance. The input impedance of the voltage buffer amplifier may be extremely high compared to other electronic elements in the data transmission system 100 as well as circuits the data transmission system 100 is designed to connect, so that an input from the first input port A may not load down the source of the input and may draw a negligible current from it. The output impedance of the voltage buffer amplifier may be low enough so that the voltage buffer circuit may drive a load, such as the first resistance element $R_1$, connected thereto as if it were a perfect voltage source. Further, the output buffer circuit $U_{IN1}$ may be a voltage buffer circuit with similar physical nature of the input buffer circuit $U_{OUT}$.

As a result, when the first input port A receives a first input signal $V_1 \sim V_2$ the forward data transmission circuit A-F-G-H-C may be able to unidirectionally transmit a data stream comprised in the first input signal $V_1 \sim V_2$ from the first input port A to the first output port C. Further, because of the large input impedance of the output voltage buffer circuit $U_{IN1}$ a current generated between A and C due to the first input signal $V_1 \sim V_2$ may be negligible.

Further, the first input signal $V_1 \sim V_2$ received at the first input port A may be a digital signal comprising a data stream under a first clock. The first clock may have a first clock frequency $f_1$. The digital signal may switch between a first voltage level $V_1$ and a second voltage level $V_2$, wherein $V_1 < V_2$.

In addition to the forward data transmission circuit A-F-G-H-C, the data transmission system 100 may include a backward data transmission circuit E-D-H-B, where D may be a second input port and B may be a second output port. The backward data transmission circuit E-D-H-B may be configured to unidirectionally transmit a data stream from the second input port D to the second output port B.

To this end, the backward data transmission circuit E-D-H-B may include a signal converter L to convert a control signal $V_3 \sim V_4$ received from a third input port E to the second input signal $V_5 \sim V_{REF}$ at the second input port D. The signal converter L may include a switch $S_1$.

The switch $S_1$ may connect the second input port D with a reference voltage level $V_{REF}$, which may be higher than the first voltage level $V_1$ of the first input signal and lower than the second voltage level $V_2$ of the first input signal, i.e., $V_1 < V_{REF} < V_2$. The switch $S_1$ may also include a control input port E to receive a control signal $V_3 \sim V_4$. The control signal $V_3 \sim V_4$ may be a digital signal comprising a data stream under a second clock. The second clock may have a second clock frequency $f_2$. The control signal $V_3 \sim V_4$ may switch between a third voltage level $V_3$ and a fourth voltage level $V_4$, where $V_3 < V_4$. $V_3$ and $V_4$ are at such voltage levels that the switch $S_1$ may change its operation status when the control signal switches from one voltage level to the other. For example, the switch $S_1$ may be close when the control signal is on the high voltage level $V_4$, the switch $S_1$ may be opened when the control signal is on the low voltage level $V_3$. Alternatively, the switch $S_1$ may be opened when the control signal is on the high voltage level $V_4$, and the switch $S_1$ may be close when the control signal is on the low voltage level $V_3$.

As a result, when the switch $S_1$ is open, there may have no current flow over the first resistance element $R_1$, or the current may be small enough that is negligible. Therefore the voltage level of points F and G may be the same or a voltage difference may be negligible or undetectable for the logic circuit $U_{IN2}$. However, when the switch $S_1$ is closed, there may be a voltage difference between F and G. Specifically, when the switch $S_1$ is closed, the second input port D may receive a voltage level of $V_{REF}$. If the voltage level of the first input signal is $V_2$, because $V_{REF} < V_2$, there will be a current flow from F towards D. As a result, the voltage level at F may be higher than the voltage level at G. Alternatively, when the switch $S_1$ is closed and the voltage level of the first input signal is $V_1$, because $V_1 < V_{REF}$, there will be a current flow from D towards F. As a result, the voltage level at G may be higher than the voltage level at F. Accordingly, the second input signal $V_5 \sim V_{REF}$ may be a digital signal switching between the reference voltage level $V_{REF}$ and a fifth voltage level $V_5$, wherein the fifth voltage $V_5$ may be equal to and synchronize with voltage levels of the first input signal $V_1 \sim V_2$.

The backward data transmission circuit may also include a logic circuit $U_{IN2}$ to detect the voltage difference over the first resistance element $R_1$, (e.g., a voltage difference between F and G) in the forward data transmission circuit A-F-G-H-C. When the voltage difference is lower than a threshold value, the logic circuit $U_{IN2}$ may output a first output voltage level $V_6$, when the voltage difference is greater than or equal to the threshold value, the logic circuit may output a second output voltage level $V_7$, which may be different from the first voltage level $V_6$. The first output voltage level $V_6$ may represent logic 1, the second voltage level $V_7$ may represent logic 0, or vice versa.

For example, the logic circuit $U_{IN2}$ may be an exclusive-OR gate. The exclusive-OR gate $U_{IN2}$ may include two inputs and one output. The two inputs may be respectively connected to points F and G, so that the corresponding voltage levels of points F and G may be sent to the exclusive-OR gate $U_{IN2}$. When the voltage level of F and the voltage level of G are different, and the difference is greater than a predetermined value, the exclusive-OR gate $U_{IN2}$ may conduct an exclusive-OR logical calculation and output a high voltage level (e.g., logic 1). Conversely, when the voltage level of F and the voltage level of G are the same or substantially the same, and the difference is zero or negligible (i.e. unable to be detected by the logic circuit), the exclusive-OR gate $U_{IN2}$ may conduct an exclusive-OR logical calculation and output a low voltage level (e.g., logic 0).

Accordingly, the backward data transmission circuit E-D-H-B may ensure that when the switch $S_1$ is open, the voltage levels of F and G are the same as the voltage level of the first input signal (i.e., $V_1$ or $V_2$), or a voltage difference between F and G is negligible or undetectable for the logic circuit $U_{IN2}$; and when the switch $S_1$ is closed, the voltage level of points F and G are different. Further, the differences between $V_1$ and $V_{REF}$, and $V_2$ and $V_{REF}$ may be big enough, so that as long as the switch $S_1$ is closed, the voltage differences between points F and G are great enough to trigger the exclusive-OR calculation of the logic circuit $U_{IN2}$. Thus with the above design, the backward data transmission may be ensured regardless if the first input signal is on a high voltage level $V_2$ or on a low voltage level $V_1$.

The backward data transmission circuit E-D-H-B may further include a second resistance element $R_2$ (e.g., a resistor) connected with the first resistance element $R_1$ and the switch $S_1$ in series. The second resistance element $R_2$ may be between the first resistance element $R_1$ and the switch $S_1$, or may be between the switch $S_1$ and the input port of the reference voltage level $V_{REF}$. For example, the second resistance element $R_2$ may be a residual resistance from the connection lines in the bidirectional data transmission system 100 or an independent circuit having a resistance. Further, the second resistance element $R_2$ may have a greater resistance than the first resistance element $R_1$ so that when the reference voltage $V_{REF}$ is applied to the reference voltage input port J, whether the switch is closed or not does not have an impact on the first input signal $V_1$~$V_2$, i.e., a data transmission on the forward data transmission circuit.

The data transmission system 100 may be a circuit built in a same piece of media, such as a silicon chip or a printed circuit board. Alternatively, the data transmission system 100 may be a combination of two or more circuits. Each circuit has an interface. A user may assemble the transmission system 100 by connecting the interfaces together, and dissemble the data transmission system 100 by disconnecting the interfaces. For example, the data transmission system 100 may be divided into two sub-circuits 102 and 104. The first sub-circuit 102 may include the buffer circuits $U_{OUT}$, $U_{IN1}$, the first resistance element $R_1$, and the logic circuit $U_{IN2}$; and the second sub-circuit 104 may include the second resistance element $R_2$ and the switch $S_1$. The first sub-circuit 102 (e.g., part of a computer circuit) and the second sub-circuit 104 (e.g., part of a U-disk) may respectively be part of different electronic devices. By connecting the first sub-circuit 102 and the second sub-circuit 104 via an interface, the two sub-circuits may be connected together to form the complete bidirectional data communication circuit 100.

Figure 2:
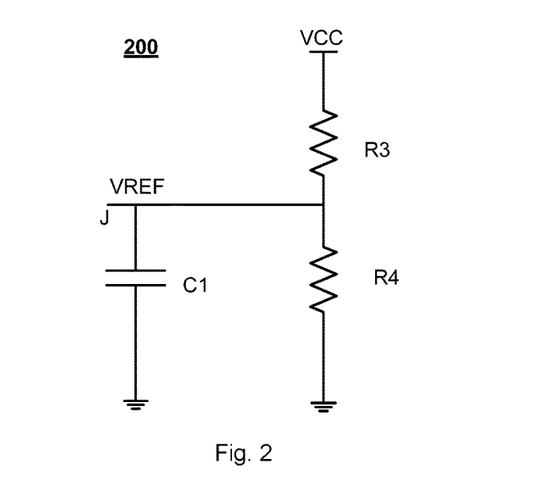
FIG. 2 illustrates a reference voltage supplying circuit according to example embodiments of the present disclosure.

The data transmission system 100 may also include a power supply circuit to provide the reference voltage $V_{REF}$. The power supply circuit may be a fast response low-dropout circuit (LDO, not shown) or DC-DC converter connected to the switch S1. Alternatively, the power supply circuit may also be a low-cost reference voltage supplying circuit 200 as shown in FIG. 2.

The reference voltage supplying circuit 200 may include a third resistance element $R_3$ (e.g., a resistor), a fourth resistance element $R_4$ (e.g., a resistor), and a capacitance element $C_1$ (e.g., a capacitor). The third resistance element $R_3$ may be connected to a power source $V_{cc}$. The capacitance element $C_1$ may be connected to the fourth resistance element $R_4$ in parallel, which may be connected to the third resistance element $R_3$ at one end and to a ground at the other end. The switch input port J may be connected to a point between the capacitor and the third resistance element $R_3$. Further, the resistances of the third resistance element $R_3$ and the fourth resistance element $R_4$ may be in such a ratio that at the voltage level $V_{REF}$ at point J may satisfy $V_1 < V_{REF} < V_2$.

When the switch $S_1$ is closed and the first input signal $V_1$~$V_2$ is at the second voltage level $V_2$, which is higher than the reference voltage level $V_{REF}$, the reference voltage supplying circuit 200 may discharge electric charges through the fourth resistance element $R_4$, i.e., a current may flow from the second resistance element $R_2$ through the fourth resistance element $R_4$. When the switch $S_1$ is closed and the first input signal is at the first voltage level $V_1$, which is lower than the reference voltage $V_{REF}$, the reference voltage supplying circuit may supply electric charges through the capacitance element $C_1$.

Figure 3:
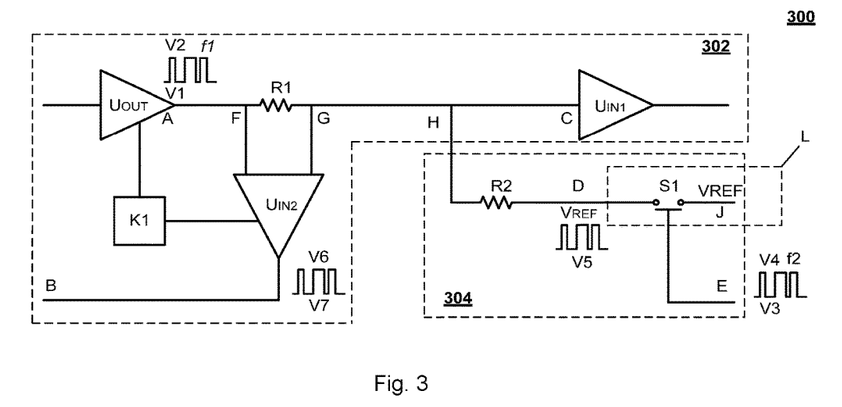
FIG. 3 illustrates another data transmission system according to example embodiments of the present disclosure.

FIG. 3 illustrates a data transmission system 300 according to example embodiments of the present disclosure. In addition to the elements in the data transmission system 100, the data transmission system 300 may further include a first control circuit $K_1$ to detect voltage level change from the first input point A and control the logic circuit $U_{IN2}$ to maintain an output during the input change.

During bidirectional data transmission, both the forward data transmission circuit A-F-G-H-C and the backward data transmission circuit E-D-H-B may be in operation and transmitting data. When the switch $S_1$ is closed, the second input port D may receive the reference voltage level $V_{REF}$. The voltage levels of points F and G may depend on whether the first input signal $V_1$~$V_2$ is on the first voltage level $V_1$ or the second voltage level $V_2$. When the first input signal $V_1$~$V_2$ is on the first voltage level $V_1$, because reference voltage level $V_{REF}$ is higher than $V_1$, a current flows over the resistance element $R_1$ from point G to point F, and the voltage level on point G is higher than the voltage level on point F. When the first input signal switches from $V_1$ to $V_2$, the current flows may reverses from point F to point G, and the voltage level of point F may become higher than the voltage level of point G. During the voltage reversing transition, there may be a moment where the voltage difference between point F and point G are small enough (e.g., when the voltage difference is in a vicinity of 0) that it may not be detectable by the logic circuit $U_{IN2}$. Thus during this moment, the output of the logic circuit $U_{IN2}$ may switch from the first output voltage level $V_6$ to the second output voltage level $V_7$.

As set forth above, the output voltage levels $V_6$~$V_7$ of the logic circuit $U_{IN2}$ should be the first output voltage level $V_6$ when the switch $S_1$ is closed, regardless of what voltage level of the first input signal. The output change from the logic circuit $U_{OUT}$ due to the voltage level change between $V_1$ and $V_2$ at the first input signal may cause an error in the backward data transmission. To eliminate the error, the first control circuit $K_1$ may be configured to connect to the buffer circuit $U_{OUT}$ or the first input port A. When the voltage level change in the first input signal is detected, the first control circuit $K_1$ may send a control signal to the logic circuit $U_{IN2}$. Upon receiving the control signal from the first control circuit $K_1$, the logic circuit $U_{IN2}$ may maintain its output prior to the voltage level change at the first input signal for a period of time until the voltage level change at the first input signal $V_1\sim V_2$ ends.

Similar to the data transmission system 100, the data transmission system 300 may be a circuit built in a same piece of media, or a combination of two or more circuits. Each circuit has an interface. A user may assemble the transmission system 300 by connecting the interfaces together, and dissemble the data transmission system 300 by disconnecting the interfaces. For example, the data transmission system 300 may be divided into two sub-circuits 302 and 304. The third sub-circuit 302 may include the buffer circuits $U_{OUT}$, $U_{IN1}$, the first resistance element $R_1$, the logic circuit $U_{IN2}$ and the first control circuit $K_1$; and the fourth sub-circuit 304 may include the second resistance element $R_2$ and the switch $S_1$. The third sub-circuit 302 (e.g., part of a computer circuit) and the fourth sub-circuit 304 (e.g., part of a U-disk) may respectively be part of two different electronic devices. By connecting the third sub-circuit 302 and the fourth sub-circuit 304 via an interface, the two sub-circuits may be connected together to form the complete bidirectional data communication circuit 300.

Figure 4:
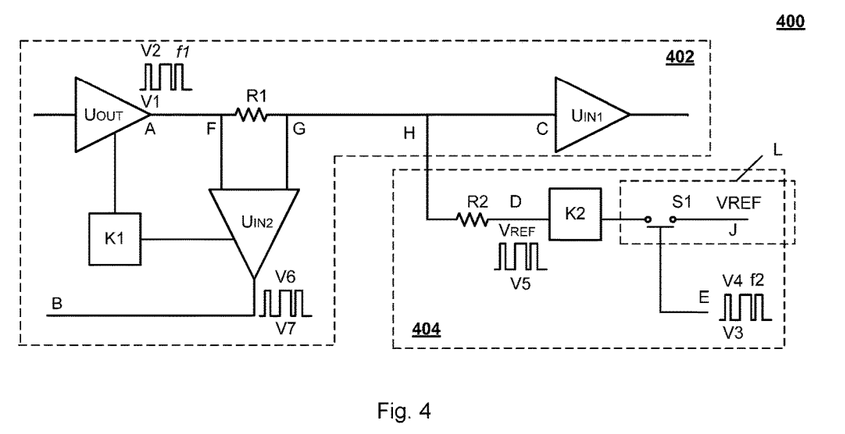
FIG. 4 illustrates yet another data transmission system according to example embodiments of the present disclosure.

FIG. 4 illustrates a data transmission system 400 according to example embodiments of the present disclosure. In addition to the elements in the data transmission system 100, the data transmission system 400 may further include the first control circuit $K_1$ as introduced in FIG. 3. The data transmission system 400 may also include a second control circuit $K_2$ connected with the control signal E, or connected to the second input port D between the second resistance element $R_2$ and the switch $S_1$. The second control circuit $K_2$ may be configured to delay the data transmission from the third input port E for a predetermined period of time and/or to modify a clock frequency of the control signal $V_3\sim V_4$, thereby delay the second input signal $V_5\sim V_{REF}$ and/or modify the corresponding clock frequency of the second input signal $V_5\sim V_{REF}$. Thus, the second control circuit $K_2$ in effect may control the delay and frequency of the second input signal $V_5\sim V_{REF}$.

When the first input signal $V_1\sim V_2$ and the second input signal $V_5\sim V_{REF}$ have the same clock frequency, error in the backward data transmission as introduced above may be able to avoid or reduced by delay the backward data transmission with a time.

Figure 5:
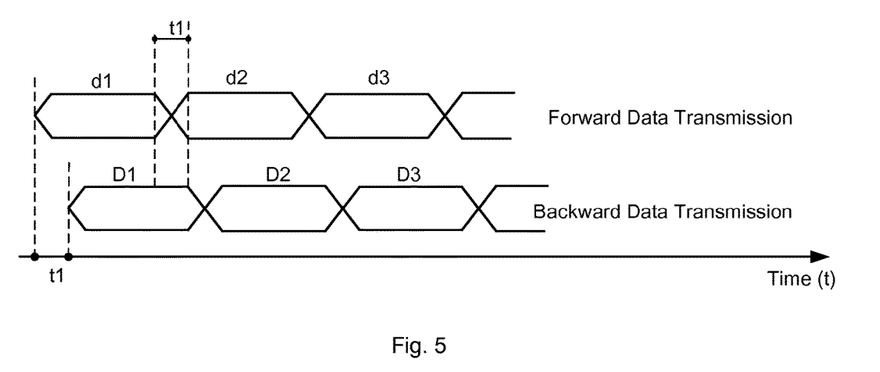
FIG. 5 illustrates a method for conducting a forward data transmission and a backward data transmission simultaneously through a data transmission system according to example embodiments of the present disclosure.

For example, FIG. 5 illustrates a method for conducting the forward data transmission and the backward data transmission when clock frequencies of the first and second input signals are equal to each other. The first input signal $V_1\sim V_2$ may include a plurality of impulse d1, d2, d3, d4, and d5. Between each pair of the impulses d1, d2, d3, there is a time $t_1$ due to the voltage jump between $V_1$ and $V_2$. The second input signal $V_5\sim V_{REF}$ may include a plurality of impulses D1, D2, D3. Because the frequency of the second input signal $V_5\sim V_{REF}$ equals the frequency of the first input signal $V_1\sim V_2$, the time that each impulse D1, D2, D3 lasts equals to the time that each impulse d1, d2, d3 lasts. The second input signal $V_5\sim V_{REF}$ may also include a time $t_1$ due to the voltage jump between $V_5$ and $V_{REF}$. As shown in FIG. 5, the second control circuit $K_2$ may receive the control signal $V_3\sim V_4$ and delay the transmission of the second input signal $V_5\sim V_{REF}$ with a predetermined time, such as a time delay equals $t_1$. As a result, when the first input signal switches between $V_1$ and $V_2$, voltage of the second input signal $V_5\sim V_{REF}$ does not switch. Because the output of the backward transmission may maintain the same value (i.e., the output of the backward transmission may freeze) when the first input signal switches voltage, the maintaining of the output $V_6\sim V_7$ and the switch of the second input signal $V_5\sim V_{REF}$ do not occur at the same time.

The first input signal and second input signal in FIG. 5 are depicted as differential signals. But one of ordinary skill in the art would understand that the method may also apply to single-ended signals.

When the clock frequency of first input signal $V_1\sim V_2$ and the clock frequency of the second input signal $V_5\sim V_{REF}$ are different but the difference is not substantial (e.g., the difference is less than 1/10 of the clock frequency of the first input signal), the second control circuit $K_2$ may modify the clock frequency $f_2$ the second input signal $V_5\sim V_{REF}$ to the same as the first clock frequency $f_1$. Then the second control circuit $K_2$ may impose a time delay to the modified second input signal as the method introduced in FIG. 5.

When the clock frequency of first input signal $V_1\sim V_2$ is much higher than the clock frequency of the second input signal $V_5\sim V_{REF}$, error in the backward data transmission introduced above may be able to avoid or reduced by delay the backward data transmission with a time when both of the first input signal and the second input signal switch voltages.

Figure 6:
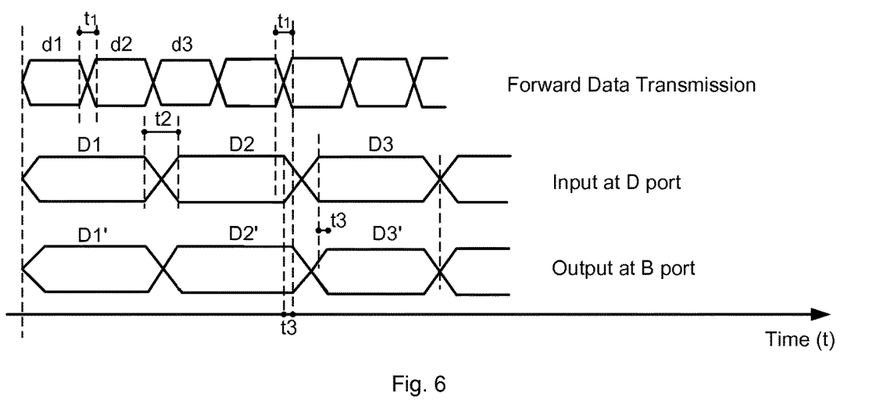
FIG. 6 illustrates another method for conducting the forward data transmission and the backward data transmission simultaneously through a data transmission system according to example embodiments of the present disclosure.

FIG. 6 illustrates a method for conducting the forward data transmission and the backward data transmission simultaneously through a data transmission system when the clock frequency $f_1$ of the first input signal $V_1\sim V_2$ is much higher (e.g., over 10 times higher) than the clock frequency $f_2$ of the second input signal $V_5\sim V_{REF}$. Accordingly, the impulse d1, d2, d3 of the first input signal may be much shorter (e.g., over 10 times shorter) than the impulse D1, D2, D3 of the second input signal; and the switching time $t_1$ of the first input signal $V_1\sim V_2$ is much shorter (e.g., more than 10 times shorter) than the switching time $t_2$ of the second input signal $V_5\sim V_{REF}$.

Because the second input signal is much slower, most of the voltage switch in the first input signal $V_1\sim V_2$ may occur when the second input signal $V_5\sim V_{REF}$ remain the same voltage, either $V_5$ or $V_{REF}$. But when the voltage switch of the first input signal $V_1\sim V_2$ overlaps with the voltage switch of the second input signal $V_5\sim V_{REF}$, the second control circuit $K_2$ may receive and maintain the voltage level of the control signal $V_3\sim V_4$ for a period of time $t_3$, thereby maintain the voltage level of the second input signal $V_5\sim V_{REF}$ for a period of time $t_3$, until the first input signal $V_1\sim V_2$ completes the voltage switch between $V_1$ and $V_2$. The second control circuit $K_2$ may let the second input signal $V_5\sim V_{REF}$ continue to transmit. Accordingly as shown in FIG. 6, the output impulse D2' that corresponds to the input impulse D2 may last a longer time of $t_3$ than D1', an output impulse corresponds to an ordinary input impulse D1. Because the second clock frequency $f_2$ of the second input signal is much lower than the first clock frequency $f_1$, an impulse of the second input signal $V_5\sim V_{REF}$ last much longer than the voltage switch time $t_1$, thus a time extension of $t_3$ may not affect the normal data transmission on the backward data transmission circuit.

The first input signal and second input signal in FIG. 6 are depicted as differential signals. But one of ordinary skill in the art would understand that the method may also apply to signal-ended signals.

When the first clock frequency $f_1$ of first input signal $V_1$~$V_2$ is much lower (e.g., 10 times lower) than the second clock frequency $f_2$ of the second input signal $V_5$~$V_{REF}$, the switching time $t_1$ of the first input signal $V_1$~$V_2$ may be long enough to send multiple impulses D1, D2, D3 of the second input signal $V_5$~$V_{REF}$ or a substantial portion of an impulse of the second input signal $V_5$~$V_{REF}$.

In such scenario, the second control circuit $K_2$ may maintain the voltage level ($V_5$ or $V_{REF}$) of the second input signal $V_5$~$V_{REF}$ for a period of time $t_3$ until the first input signal $V_1$~$V_2$ completes the voltage switch. During this period of time $t_3$, the second control circuit $K_2$ may hold off the data transmission on the backward data transmission circuit. For example, the second control circuit $K_2$ may hold off the second input signal $V_5$~$V_{REF}$. When the first input signal $V_1$~$V_2$ completes the voltage switch, the second control circuit $K_2$ may resume the data transmission, e.g., resume sending the second input signal $V_5$~$V_{REF}$ into the backward data transmission circuit, thereby avoiding the error due to the voltage switch occurred in the forward data transmission circuit.

Similar to the data transmission system 100, the data transmission system 400 may be a circuit built in a same piece of media, or a combination of two or more circuits. Each circuit has an interface. A user may assemble the transmission system 400 by connecting the interfaces together, and dissemble the data transmission system 400 by disconnecting the interfaces. For example, the data transmission system 400 may be divided into two sub-circuits 402 and 404. The fifth sub-circuit 402 may include the buffer circuits $U_{OUT}$, $U_{IN1}$, the first resistance element $R_1$, the logic circuit $U_{IN2}$ and the first control circuit $K_1$; and the sixth sub-circuit 304 may include the second resistance element $R_2$, the switch $S_1$, and the second control circuit $K_2$. The fifth sub-circuit 402 (e.g., part of a computer circuit) and the sixth sub-circuit 404 (e.g., part of a U-disk) may respectively be part of two different electronic devices. By connecting the fifth sub-circuit 402 and the sixth sub-circuit 404 via an interface, the two sub-circuits may be connected together to form the complete bidirectional data communication circuit 400.

Figure 7:
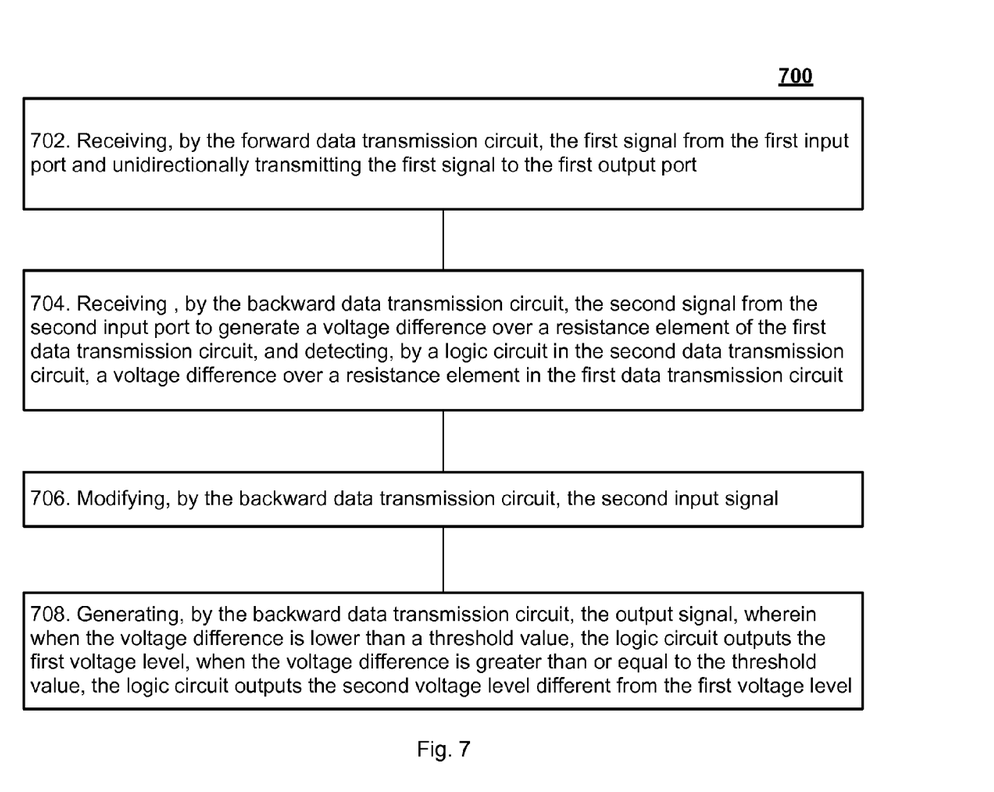
FIG. 7 is a flowchart illustrating a method for conducting bidirectional data transmission according to example embodiments of the present disclosure.

FIG. 7 is a flowchart illustrating a method for conducting bidirectional data transmission according to example embodiments of the present disclosure. The method may be implemented by the bidirectional data transmission systems as shown in FIGS. 1, 3, and 4. The method may include the follow operations:

Operation 702. Receiving, by the forward data transmission circuit A-F-G-H-C, the first input signal from the first input port and unidirectionally transmitting the first input signal to the first output port.

Operation 704. Receiving, by the backward data transmission circuit E-D-H-B, the second input signal from the second input port D to generate the voltage difference over the resistance element $R_1$ of the forward data transmission circuit, wherein the backward data transmission circuit E-D-H-B comprises the logic circuit $U_{IN2}$ to detect a voltage difference over the resistance element $R_1$ in the forward data transmission circuit.

Detecting, by a logic circuit in the backward data transmission circuit, a voltage difference over a resistance element in the forward data transmission circuit, Operation 706. Modifying, by the backward data transmission circuit, the second input signal and the corresponding output signal. The second input signal may be modified by the second control circuit $K_2$ and the output signal may be modified by the first control circuit $K_1$, as set forth above.

Operation 708. Generating, by the backward data transmission circuit, the output signal, wherein when the voltage difference is lower than a threshold value, the logic circuit outputs the first voltage level, when the voltage difference is greater than or equal to the threshold value, the logic circuit outputs the second voltage level different from the first voltage level.

While example embodiments of the present disclosure relate to systems and methods for bidirectional data transmission for a USB, the systems and methods may also be applied to other Applications, such as other hardware transmission channels. FIGS. 1, 3, and 4 illustrate the bidirectional data transmission systems designs based on single-ended data transmission. One of ordinary skill in the art would understand that the same systems may also be easily used in a differential data transmission system. Also, FIGS. 1, 3, and 4 illustrate the bidirectional data transmission systems designs based on parallel transmission ports. One of ordinary skill in the art would understand that the same designs may be easily adopted by a serial data transmission port. The systems are illustrated as independent circuits but it is the intention of the present disclosure to include any circuit designs that incorporate the circuits therein. The present disclosure intends to cover the broadest scope of systems and methods that implemented the invention in the present disclosure.

Thus, example embodiments illustrated in FIGS. 1-7 serve only as examples to illustrate several ways of implementation of the present disclosure. They should not be construed as to limit the spirit and scope of the example embodiments of the present disclosure. It should be noted that those skilled in the art may still make various modifications or variations without departing from the spirit and scope of the example embodiments. Such modifications and variations shall fall within the protection scope of the example embodiments, as defined in attached claims.

The invention claimed is:

1. A system for bidirectional signal transmission, comprising:
    a forward data transmission circuit to receive a first input signal from a first input port and transmit the first input signal to a first output port; and
    a backward data transmission circuit to receive a second input signal from a second input port and transmit the second input signal to a second output port, the backward data transmission circuit comprising:
    a logic circuit to detect a voltage difference over a first resistance element in the forward data transmission circuit, wherein:
        when the voltage difference is lower than a threshold value, the logic circuit outputs a first output voltage level, and
        when the voltage difference is greater than or equal to the threshold value, the logic circuit outputs a second output voltage level different from the first output voltage level.

2. The system of claim 1, wherein:
    the first input signal is a digital signal switching between a first voltage level and a second voltage level lower than the first voltage level; and the second input signal is a digital signal switching between a reference voltage level and a third voltage level, wherein:
the third voltage level synchronizes with the first input signal and equals to a voltage level of the first input signal, and
the reference voltage level is lower than the first voltage level and higher than the second voltage level.

3. The system of claim 2, further comprising:
a first control circuit to detect an input voltage change from the first input port and control the logic circuit to maintain an output during the input voltage change.

4. The system of claim 3, wherein:
the first input signal is associated with a first clock frequency,
the second input signal is associated with a second clock frequency,
the first input signal comprises a first switch time between each switch between the first voltage level and the second voltage level, and
the second input signal comprises a second switch time when switching between the reference voltage level and the third voltage level.

5. The system of claim 4, further comprising a second control circuit to modify the second input signal, wherein
when the second clock frequency is more than ten times higher than the first clock frequency and the first switch time overlaps with the second switch time, the second control circuit holds off the second input signal and the first control circuit controls the logic circuit to maintain the output until the input voltage change of the first input signal is completed,
when a difference between the first clock frequency and the second clock frequency is smaller than one tenth of the first clock frequency, the second control circuit modifies the second clock frequency in the second input signal to the first clock frequency,
when the second clock frequency equals the first clock frequency, the second control circuit transmits the second input signal with a time delay that equals the first switch time, and
when the first clock frequency is more than ten times higher than the second clock frequency and the first switch time overlaps with the second switch time, the second control circuit holds off the second input signal and the first control circuit controls the logic circuit to maintain the output until the input voltage change of the first input signal is completed.

6. The system of claim 1, wherein the forward data transmission circuit comprises:
a first buffer circuit connected to the first input port; and
a second buffer circuit connected to the first output port, wherein:
the first resistance element is between the first buffer circuit and the second buffer circuit, and
a first port of the first resistance element is connected to the first buffer circuit and a second port of the first resistance element is connected to the second buffer circuit.

7. The system of claim 6, wherein:
the first buffer circuit comprises a power amplifier,
the second buffer circuit comprises a power amplifier, and
the logic circuit comprises an exclusive-OR gate.

8. The system of claim 1, further comprising a switch connected to the second input port, the switch comprising:

a switch input port to receive a reference voltage, wherein:
the first input signal is a digital signal switching between a first voltage level and a second voltage level lower than the first voltage level, and
the reference voltage is lower than the first voltage level and higher than the second voltage level;
a switch output port connected to the first resistance element; and
a switch control port to receive a control signal.

9. The system of claim 8, wherein
the control signal is a digital signal switching between a third voltage level and a fourth voltage level,
the switch opens when the control signal switches to the third voltage level, and
the switch closes when the control signal switches to the fourth voltage level.

10. The system of claim 8, wherein the backward data transmission circuit further comprises a second resistance element connected to the switch in series between the switch output port and the first resistance element,
wherein the second resistance element has a greater resistance than the first resistance element so that when the reference voltage is applied to the switch input port and the first input signal is applied to the first input port, whether the switch is closed or not does not have an impact on a data transmission between the first input port and the first output port.

11. The system of claim 8, wherein the switch input port connects to a fast response low-dropout circuit.

12. The system of claim 8, further comprising:
a third resistance element connected to an power source;
a fourth resistance element connected to the third resistance element in series and a ground; and
a capacitor connected with the fourth resistance element in parallel between the third resistance element and the ground,
wherein the switch input port connects to a point between the capacitor and the third resistance element.

13. A method for bidirectional data transmission, comprising:
receiving, by a forward data transmission circuit, a first input signal from a first input port and transmitting the first input signal to a first output port;
receiving, by a backward data transmission circuit, a second input signal from a second input port to generate a voltage difference over a resistance element of the forward data transmission circuit;
detecting, by a logic circuit in the backward data transmission circuit, the voltage difference over the resistance element in the forward data transmission circuit, wherein:
when the voltage difference is lower than a threshold value, the logic circuit outputs a first output voltage level, and
when the voltage difference is greater than or equal to the threshold value, the logic circuit outputs a second output voltage level different from the first output voltage level; and
generating, by the backward data transmission circuit, an output signal.

14. The method of claim 13, wherein:
the first input signal is a digital signal switching between a first voltage level and a second voltage level lower than the first voltage level, and
the second input signal is a digital signal switching between a reference voltage level and a third voltage level, wherein the third voltage level synchronizes with the first input signal and equals to a voltage level of the first input signal.

15. The method of claim 14, wherein the reference voltage level is lower than the first voltage level and higher than the second voltage level.

16. The method of claim 14, wherein:
the first input signal is associated with a first clock frequency,
the second input signal is associated with a second clock frequency,
the first input signal comprises a first switch time between each switch between the first voltage level and the second voltage level, and
the second input signal comprises a second switch time when switching between the reference voltage level and the third voltage level.

17. The method of claim 16, further comprising:
detecting, by a first control circuit, a voltage change of the first input signal when the first input signal switches between the first voltage level and the second voltage level; and
maintaining, by the backward data transmission circuit, the output signal when the voltage change is detected.

18. The method of claim 17, further comprising:
when the second clock frequency is more than ten times higher than the first clock frequency and the first switch time overlaps with the second switch time, holding off the second input signal and maintaining the output signal until the voltage change of the first input signal is completed;
when a difference between the first clock frequency and the second clock frequency is smaller than one tenth of the first clock frequency, modifying the second clock frequency in the second input signal to the first clock frequency;
when the second clock frequency equals the first clock frequency, transmitting the second input signal with a time delay that equals the first switch time; and
when the first clock frequency is more than ten times higher than the second clock frequency and the first switch time overlaps with the second switch time, holding off the second input signal and maintaining the output signal until the voltage change of the first input signal is completed.

19. The method of claim 17, further comprising:
when the second clock frequency equals the first clock frequency, transmitting the second input signal with a time delay that equals the first switch time.

20. A method for bidirectional data transmission, comprising:
receiving, by a forward data transmission circuit, a first input signal from a first input port and unidirectionally transmitting the first input signal to a first output port;
receiving, by a backward data transmission circuit, a second input signal from a second input port to generate a voltage difference over a resistance element of the forward data transmission circuit;
detecting, by a logic circuit in the backward data transmission circuit, the voltage difference over the resistance element in the forward data transmission circuit, wherein:
when the voltage difference is lower than a threshold value, the logic circuit outputs a first output voltage level, and
when the voltage difference is greater than or equal to the threshold value, the logic circuit outputs a second output voltage level different from the first output voltage level; and
generating, by the backward data transmission circuit, an output signal.

* * * * *